United States Patent
Niikura et al.

[11] Patent Number: 6,106,994
[45] Date of Patent: Aug. 22, 2000

[54] PRODUCTION PROCESS OF POLYPHENOL DIESTERS, AND POSITIVE PHOTOSENSITIVE COMPOSITIONS

[75] Inventors: Satoshi Niikura; Hidekatsu Kohara; Toshimasa Nakayama, all of Kanagawa, Japan

[73] Assignee: Tokyo Ohka Kogyo Co., Ltd., Kanagawa, Japan

[21] Appl. No.: 09/210,716

[22] Filed: Dec. 14, 1998

[30] Foreign Application Priority Data

Dec. 15, 1997 [JP] Japan ..................... 9-345274
Jan. 26, 1998 [JP] Japan ..................... 10-012421

[51] Int. Cl.[7] .......................... G03C 1/492; C07C 50/08; C07C 303/00
[52] U.S. Cl. ................ 430/270.1; 430/192; 552/292; 558/56; 558/58
[58] Field of Search .................... 430/189, 192; 558/58, 56; 552/292

[56] References Cited

U.S. PATENT DOCUMENTS

| | | | |
|---|---|---|---|
| 3,188,210 | 6/1965 | Fritz et al. | 96/33 |
| 4,732,836 | 3/1988 | Potvin et al. | 430/192 |
| 5,114,816 | 5/1992 | Scheler et al. | 430/192 |
| 5,407,778 | 4/1995 | Uetani et al. | 430/192 |
| 5,413,899 | 5/1995 | Scheler et al. | 430/326 |
| 5,478,361 | 12/1995 | Miyashita et al. | 430/190 |
| 5,529,881 | 6/1996 | Kawabe et al. | 430/191 |
| 5,534,382 | 7/1996 | Kawabe et al. | 430/192 |
| 5,639,587 | 6/1997 | Sato et al. | 430/190 |
| 5,965,320 | 10/1999 | Torimitsu et al. | 430/192 |

FOREIGN PATENT DOCUMENTS

| | | | |
|---|---|---|---|
| 0706089 | 4/1996 | European Pat. Off. | G03F 7/022 |
| 9-114094 | 5/1997 | Japan . | |

*Primary Examiner*—Janet Baxter
*Assistant Examiner*—Rosemary Ashton
*Attorney, Agent, or Firm*—Sughrue, Mion, Zinn, Macpeak & Seas, PLLC

[57] ABSTRACT

A process for producing a polyphenol diester comprises esterifying a polyphenol compound and a naphthoquinone-1,2-diazidesulfonyl halide in the presence of for example monomethyldicyclohexylamine, and a positive photosensitive composition contains the resultant ester. According to this process, a diester of any polyphenol compound can be obtained with ease in a good yield, and a composition using the diester can achieve a high definition and a satisfactory exposure margin.

6 Claims, No Drawings

PRODUCTION PROCESS OF POLYPHENOL DIESTERS, AND POSITIVE PHOTOSENSITIVE COMPOSITIONS

BACKGROUND OF THE INVENTION

1. Field of the Invention

The present invention relates to a process for producing a polyphenol diester (hereinafter simply referred to diester) by esterifying a polyphenol compound having 2 to 10 phenolic hydroxyl group and having a molecular weight of equal to or less than 1,000 with a naphthoquinone-1,2-diazidesulfonyl halide. It also relates to a positive photosensitive composition using this diester.

2. Description of the Related Art

Positive photoresist compositions each comprising an alkali-soluble resin and a quinonediazide group-containing compound (photosensitizer) are excellent in definition, sensitivity and etching resistance and hence have been used for the production of semiconductor devices and liquid crystal devices.

Photosensitizer used in such positive photoresist compositions can usually be obtained by esterifying a polyphenol compound having 2 to 10 hydroxyl groups and having a molecular weight of equal to or less than 1,000 with a naphthoquinone-1,2-diazidesulfonyl halide.

These conventional photosensitizers, however, comprise different types of esters (e.g., monoesters, diesters and triesters) and hence may respond to light unequally or have a deteriorated contrast.

Japanese Patent Laid-Open No. 2-19846 discloses a positive photoresist composition which employs a photosensitizer comprising more than 50% of a diester relative to quinonediazidesulfonic esters of a phenol compound. This conventional technique may provide a high definition since the photosensitizer contains a large proportion of the diester, but it requires the use of a halogen-containing solvent such as chloroform, trichloroethane, trichloroethylene and dichloroethane and such a solvent adversely affects the environment. The literature also refers to the production of a diester in the presence of triethylamine, but such a diester as produced in the presence of triethylamine cannot provide an intended definition and exposure margin, as described in detail below.

Japanese Patent Laid-Open No. 6-167805 and No. 8-339079 each discloses a photosensitizer comprising an increased proportion of the diester. These techniques, however, require the use of polyphenol compounds each having a specific skeleton, and they cannot be applied to any other polyphenol compounds than the specific polyphenol compounds.

Japanese Patent Laid-Open No. 7-261382 discloses a technique of increasing the proportion of a diester by using a basic catalyst such as alicyclic amines including, for example, 4-methylmorpholine, N-methylpiperazine and N-methylpiperidine. The basic catalysts used in this technique are different from those of the present invention, and in addition, the technique also requires the use of polyphenol compounds each having a specific skeleton and cannot be applied to any other polyphenol compounds.

In addition, as the basic catalysts, there are known ethylamine, ethanolamine, diethylamine, diisopropylamine, diethanolamine, dicyclohexylamine and other primary or secondary amines, and trimethylamine, tripropylamine and other tertiary amines each having a lower alkyl group. With any of these basic catalysts, however, a diester cannot be selectively produced from any of various polyphenol compounds.

SUMMARY OF THE INVENTION

Accordingly, it is an object of the present invention to provide a process for producing a polyphenol diester in which, without using a polyphenol compound having a specific skeleton, a diester of any polyphenol compound having 2 to 10 phenolic hydroxyl groups and having a molecular weight of equal to or less than 1,000 can be obtained with ease and in a high yield and, through the function of the diester, a high definition and a satisfactory exposure margin can be obtained, and to provide a positive photosensitive composition using the polyphenol diester.

After intensive investigations, the present inventors found that the above object can be achieved by esterifying a polyphenol compound having 2 to 10 phenolic hydroxyl groups and having a molecular weight of equal to or less than 1,000 with a naphthoquinone-1,2-diazidesulfonyl halide in the presence of a specific nitrogen-containing basic catalyst. The present invention has been accomplished based on the above finding.

To be more specific, the present invention provides a process for producing a polyphenol diester which comprises the step of esterifying a polyphenol compound having 2 to 10 phenolic hydroxyl groups and having a molecular weight of equal to or less than 1,000 with a naphthoquinone-1,2-diazidesulfonyl halide in the presence of a compound represented by the following formula (I) or (II):

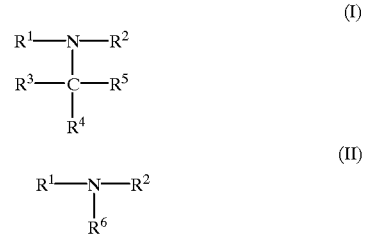

where each of $R^1$, $R^3$, $R^4$ and $R^5$ is independently an alkyl group, alkenyl group or alkoxy group each having from 1 to 4 carbon atoms, $R^2$ is an alkyl group, alkenyl group or alkoxy group each having from 1 to 10 carbon atoms or a cycloalkyl group having from 3 to 10 carbon atoms, and $R^6$ is an alkyl group or cycloalkyl group each having from 5 to 10 carbon atoms.

In another aspect the invention provides the aforementioned process, in which the compound represented by the formula (II) is a compound represented by the following formula (III):

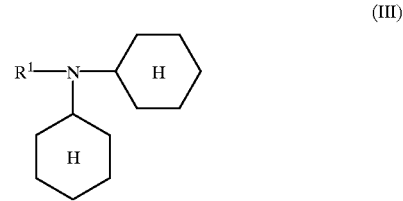

where $R^1$ has the same meaning as defined above.

In addition, the invention provides a positive photosensitive composition comprising (A) an alkali-soluble resin, and (B) a polyphenol diester produced by the aforementioned production process.

DETAILED DESCRIPTION OF THE INVENTION

The compounds represented by the formula (I) or (II) are tertiary amines and have at least one of the following group (IV) or (V) being directly bonded to its nitrogen atom.

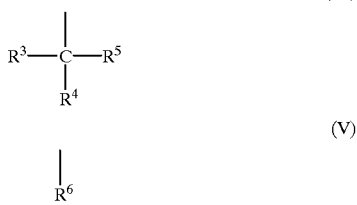

As described above, the use of conventionally known amines cannot selectively provides a diester of any various polyphenol compounds. Such conventional amines include primary or secondary amines such as ethylamine, ethanolamine, diethylamine, diisopropylamine, diethanolamine and dicyclohexylamine, and tertiary amines containing a lower alkyl group such as trimethylamine, triethylamine and tripropylamine. In addition, the use of a primary or secondary amine tends to invite the formation of by-products.

As known amines having an aromatic hydrocarbon group, there may be mentioned for example N,N-dimethylaniline and N,N-diethylaniline. These compounds have, however, little basicity and little activity as catalysts, and hence are not preferable in the present invention.

In the formula (I) and (II), each of $R^1$, $R^3$, $R^4$ and $R^5$ is independently an alkyl group having from 1 to 4 carbon atoms such as methyl, ethyl, propyl and butyl groups; an alkenyl group having from 2 to 4 carbon atoms such as vinyl, propenyl and butenyl groups; or an alkoxy group having from 1 to 4 carbon atoms such as methoxy, ethoxy, propoxy and butoxy groups. The substituent $R^2$ is an alkyl group having from 1 to 10 carbon atoms such as methyl, ethyl, propyl, butyl, pentyl, hexyl, heptyl, octyl, nonyl and decyl groups; an alkenyl group having from 2 to 10 carbon atoms such as vinyl, propenyl, butenyl, pentenyl, hexenyl, heptenyl, octenyl, nonenyl and decenyl groups; an alkoxy group having from 1 to 10 carbon atoms such as methoxy, ethoxy, propoxy, butoxy, pentyloxy, hexyloxy, heptyloxy, octyloxy, nonyloxy and decyloxy groups; or a cycloalkyl group having from 3 to 10 carbon atoms such as cyclopropyl, cyclobutyl, cyclopentyl, cyclohexyl, cycloheptyl, cyclooctyl, cyclononyl and cyclodecyl groups; and $R^6$ is an alkyl group having from 5 to 10 carbon atoms such as pentyl, hexyl, heptyl, octyl, nonyl, and decyl groups, or a cycloalkyl group having from 5 to 10 carbon atoms such as cyclopentyl, cyclohexyl, cycloheptyl, cyclooctyl, cyclononyl and cyclodecyl groups.

As practical examples of the compounds represented by the formula (I), there may be mentioned monoethylditert-butylamine, N,N-dimethyl-1,1-dimethylpropylamine, N-ethyl-N-methyl-1,1-methylethyl-butylamine, N-cyclohexyl-N-ethyl-1,1-diethyl-pentylamine, N-ethoxy-N-propyl-1,1-diethyl-pentylamine and the like. The typical examples of the compounds represented by the formula (II) include monomethyldicyclohexylamine, monocyclohexyldiethylamine, N-ethyl-N-cyclohexyl-hexylamine, N-ethyl-N-methoxy-hexylamine, N-cyclohexyl-N-propyl-heptylamine and the like. Each of these compounds can be used singly or in combination.

Among them, the compounds represented by the formula (III) are preferred, of which monomethyldicyclohexylamine is typically preferred.

The amount of the compound represented by the formula (I) or (II) should preferably fall in the range from 0.8 to 4.0 moles and more preferably from 1.0 to 2.2 moles per mole of a naphthoquinone-1, 2-diazidesulfonyl halide (hereinafter simply referred to as NQD). The use of the compound within this range decreases unreacted NQD, further enhances the selectivity of diesterification and hence reduces the risk of remaining of an amine in the produced ester. The polyphenol compound having 2 to 10 phenolic hydroxyl groups and having a molecular weight of equal to or less than 1,000 used in the invention is not specially restricted and can be selected from those conventionally used as photosensitizers in positive photosensitive compositions.

Examples of the polyphenol compounds include 2,3,4-trihydroxybenzophenone, 2,4,4'-trihydroxybenzophenone, 2,4,6-trihydroxybenzophenone, 2,3,4,4'-tetrahydroxybenzophenone, 2,2',4,4'-tetrahydroxybenzophenone, 2,3',4,4'6-pentahydroxybenzophenone, 2,2',3,4,4'-pentahydroxybenzophenone, 2,2',3,4,5'-pentahydroxybenzophenone, 2,3',4,5,5'-pentahydroxybenzophenone, 2,3,3',4,4',5'-hexahydroxybenzophenone and other benzophenone compounds; bis[2-hydroxy-3-(2-hydroxy-5-methylbenzyl)-5-methylphenyl]methane, bis[2,5-dimethyl-3-(2-hydroxy-5-methylbenzyl)-4-hydroxyphenyl]methane, bis[2,5-dimethyl-3-(4-hydroxy-3-methylbenzyl)-4-hydroxyphenyl]methane, tris(4-hydroxyphenyl)methane, bis(4-hydroxy-3,5-dimethylphenyl)-4-hydroxyphenylmethane, bis(4-hydroxy-3,5-dimethylphenyl)-3-hydroxyphenylmethane, bis(4-hydroxy-3,5-dimethylphenyl)-2-hydroxyphenylmethane, bis(4-hydroxy-2,5-dimethylphenyl)-4-hydroxyphenylmethane, bis(4-hydroxy-2,5-dimethylphenyl)-3-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)- 3,4-dihydroxyphenylmethane, bis(4-hydroxy-3,5-dimethylphenyl)-2,4-dihydroxyphenylmethane, bis(4-hydroxy-2,5-dimethylphenyl)-2,4-dihydroxyphenylmethane, bis(4-hydroxyphenyl)-3-methoxy-4-hydroxyphenylmethane, bis (3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(3-cyclohexyl-4-hydroxy-6-methylphenyl)-2-hydroxyphenylmethane, bis(3-cyclohexyl-4-hydroxy-6-methylphenyl)-3-hydroxyphenylmethane, bis(3-cyclohexyl-4-hydroxy-6-methylphenyl)-4-hydroxyphenylmethane, bis (3-cyclohexyl-4-hydroxy-6-methylphenyl)-3,4-dihydroxyphenylmethane, bis(3-cyclohexyl-6-hydroxyphenyl)-3-hydroxyphenylmethane, bis(3-cyclohexyl-6-hydroxyphenyl)-4-hydroxyphenylmethane, bis(3-cyclohexyl-6-hydroxyphenyl)-2-hydroxyphenylmethane, bis(3-cyclohexyl-6-hydroxy-4-methylphenyl)-2-hydroxyphenylmethane, bis (4-hydroxy-2-methyl-5-cyclohexylphenyl)-3,4-dihydroxyphenylmethane, bis (3-cyclohexyl-6-hydroxy-4-methylphenyl)-4-hydroxyphenylmethane, bis(3-cyclohexyl-6-hydroxy-4-methylphenyl)-3,4-dihydroxyphenylmethane, 1-[1-(4-hydroxyphenyl)isopropyl]-4-[1,1-bis(4-hydroxyphenyl)ethyl]benzene, 1-[1-(3-methyl-4-hydroxyphenyl)isopropyl]-4-[1,1-bis(3-methyl-4-hydroxyphenyl)ethyl]benzene, bis(4-hydroxy-2,3,5-trimethylphenyl)-2-hydroxyphenylmethane, bis(4-hydroxy- 2,3,5-trimethylphenyl)-3-hydroxyphenylmethane, bis(4-hydroxy-2,3,5-trimethylphenyl)-4-hydroxyphenylmethane, bis(4-hydroxy-2,3,5-trimethylphenyl)-3,4-dihydroxyphenylmethane, bis(4- hydroxy-2,3,5-trimethylphenyl)-4-hydroxy-3-methoxyphenylmethane and other hydroxyaryl compounds; 2-(2,3,4-trihydroxyphenyl)-2-(2',3',4'-trihydroxyphenyl) propane, 2-(2,4-dihydroxyphenyl)-2-(2',4'-dihydroxyphenyl)propane, 2-(4-hydroxyphenyl)-2-(4'-hydroxyphenyl)propane, bis(2,3,4-trihydroxyphenyl) methane, bis(2,4-dihydroxyphenyl)methane and other bis(hydroxyphenyl)alkane compounds; 1,1-bis(4-hydroxyphenyl)cyclohexane, 1,1-bis(2-methyl-4-hydroxyphenyl)cyclohexane and other bis(hydroxyphenyl) cycloalkane compounds; 2,6-bis[1-(2,4-dihydroxyphenyl) isopropyl]-4-methylphenol, 4,6-bis[1-(4-hydroxyphenyl) isopropyl]resorcin, 4,6-bis(3,5-dimethoxy-4-hydroxyphenylmethyl)pyrogallol, 2,6-bis(3,5-dimethyl-4,6-dihydroxyphenylmethyl)-4-methylphenol, 2,6-bis(2,3,4-trihydroxyphenylmethyl)-4-methylphenol and the like; hydroquinone, bisphenol A, pyrocatechol, pyrogallol monomethyl ether, gallic acid, partially-esterified or partially-etherified gallic acid derivatives; 2,4-bis[2-hydroxy-3-(4-hydroxybenzyl)-5-methylbenzyl]-6-cyclohexylphenol, 2,4-bis[2-hydroxy-3-(4-hydroxybenzyl)-5-ethylbenzyl]-6-cyclohexylphenol, 2,4-bis[2-hydroxy-3-(4-hydroxybenzyl)-5-propylbenzyl]-6-cyclohexylphenol, 2,4-bis[2-hydroxy-3-(4-hydroxybenzyl)-5-methoxybenzyl]-6-cyclohexylphenol, 2,4-bis[2-hydroxy-3-(4-hydroxybenzyl)-5-ethoxybenzyl]-6-cyclohexylphenol, 2,4-bis[2-hydroxy-3-(4-hydroxybenzyl)-5-ethenylbenzyl]-6-cyclohexylphenol, 2,4-bis[2-hydroxy-3-(3-hydroxybenzyl)-5-methylbenzyl]-6-cyclohexylphenol, 2,4-bis[2-hydroxy-3-(5-hydroxybenzyl)-5-methylbenzyl]-6-cyclohexylphenol, 2,4-bis[4-hydroxy-3-(4-hydroxybenzyl)-5-methylbenzyl]-6-cyclohexylphenol, 2,4-bis[4-hydroxy-3-(4-hydroxybenzyl)-5-ethylbenzyl]-6-cyclohexylphenol, 2,4-bis[4-hydroxy-3-(4-hydroxybenzyl)-5-propylbenzyl]-6-cyclohexylphenol, 2,4-bis[4-hydroxy-3-(4-hydroxybenzyl)-5-methoxybenzyl]-6-cyclohexylphenol, 2,4-bis[4-hydroxy-3-(4-hydroxybenzyl)-5-ethoxybenzyl]-6-cyclohexylphenol, 2,4-bis[4-hydroxy-3-(4-hydroxybenzyl)-5-ethenylbenzyl]-6-cyclohexylphenol, 2,4-bis[4-hydroxy-3-(4-hydroxybenzyl)-5-methylbenzyl]-3-methyl-6-cyclohexylphenol, 2,4-bis[4-hydroxy-3-(4-hydroxybenzyl)-5-ethylbenzyl]-3-methyl-6-cyclohexylphenol, 2,4-bis[4-hydroxy-3-(4-hydroxybenzyl)-5-methoxybenzyl]-3-methyl-6-cyclohexylphenol, 2,4-bis[4-hydroxy-3-(4-hydroxybenzyl)-5-ethenylbenzyl]-3-methyl-6-cyclohexylphenol, 2,4-bis[4-hydroxy-3-(4-hydroxybenzyl)-5-methylbenzyl]-3-ethyl-6-cyclohexylphenol, 2,6-bis[4-hydroxy-3-(4-hydroxybenzyl)-5-methylbenzyl]-4-cyclohexylphenol, 2,6-bis[4-hydroxy-3-(4-hydroxybenzyl)-5-ethylbenzyl]-4-cyclohexylphenol, 2,6-bis[4-hydroxy-3-(4-hydroxybenzyl)-5-methoxybenzyl]-4-cyclohexylphenol, 2,6-bis[4-hydroxy-3-(4-hydroxybenzyl)-5-ethenylbenzyl]-4-cyclohexylphenol, 2,6-bis[2-hydroxy-3-(4-hydroxybenzyl)-5-methylbenzyl]-4-cyclohexylphenol, 2,6-bis[2-hydroxy-3-(4-hydroxybenzyl)-5-ethylbenzyl]-4-cyclohexylphenol, 2,6-bis[2-hydroxy-3-(4-hydroxybenzyl)-5-methoxybenzyl]-4-cyclohexylphenol, 2,6-bis[2-hydroxy-3-(4-hydroxybenzyl)-5-ethenylbenzyl]-4-cyclohexylphenol and the like.

NQD used here is not specially limited and can be chosen from among those generally used in photosensitive compositions. Preferred examples of NQD include naphthoquinone-1,2-diazide-5-sulfonyl chloride, naphthoquinone-1,2-diazide-4-sulfonyl chloride, naphthoquinone-1,2-diazide-6-sulfonyl chloride and other naphthoquinone-1,2-diazidesulfonyl halides.

The esterification of the polyphenol compound with NQD may be conducted in the following manner: Initially, the polyphenol compound and NQD are dissolved in a solvent, and the compound represented by the formula (I) or (II) (catalyst) as dissolved in a solvent is added to the resulting solution; or the polyphenol compound and the catalyst are dissolved in a solvent and to this solution is added NQD dissolved in a solvent. Subsequently the mixture is stirred for 1 to 5 hours. The addition should preferably be carried out by adding dropwise at a temperature of about −5° C. to 35° C. over about 1 to 150 minutes.

Next, the reaction solution or a filtrate obtained by filtering the reaction solution to remove a precipitate is then poured into a large quantity of pure water to precipitate an ester. The precipitated ester is washed with pure water or an aqueous dilute acid solution and dried to be supplied for the preparation of a positive photosensitive composition. Before poured into a large quantity of pure water, the reaction solution or its filtrate may be neutralized with an acid in advance.

The solvent used in the above reaction is not particularly limited, and any of known solvents for esterification such as ethers, lactones, aliphatic ketones or the like can be employed. Practical examples of such solvents include dioxolane, 1,4-dioxane, tetrahydrofuran, γ-butyrolactone, acetone, 2-heptanone, propylene glycol monomethyl ether, N-methylpyrrolidone, water, diethylene glycol dimethyl ether and the like.

Each of these solvents can be used singly or in combination.

NQD is preferably added in an amount of about 2 moles per mole of the polyphenol compound for the selective formation of a diester. When the amount of NQD is about 1 mole per mole of the polyphenol compound, a monoester is liable to be formed, whereas when it is about 3 moles, a triester tends to be formed. These situations should be avoided.

Although the product contains a monoester and triester in addition to a diester, it is rich in the diester and hence the product is referred to as "diester" herein. The diester can be incorporated as a photosensitizer into a positive photosensitive composition. In other word, the invention provides a positive photosensitive composition (A) an alkali-soluble resin and (B) the diester, which is excellent in definition and exposure margin.

The proportion of the diester (B) may fall in the range from 10 to 60% by weight and preferably from 20 to 50% by weight relative to the total weight of the alkali-soluble resin (A) and an intensifier (sense amplifier) added where necessary. The incorporation of the diester (B) within this range provides more enhanced advantages of the present invention such as the definition and exposure margin, and further enhances film residual rate, development contrast, focal depth range properties, sectional shape and other properties. A blend of diesters respectively obtained from different polyphenol compounds can also be employed as the diester.

The alkali-soluble resin as the ingredient (A) is not restricted and can arbitrarily be selected from those generally used as film-forming substances in positive photosensitive compositions.

By way of illustration, condensates of aromatic hydroxy compounds and aldehydes or ketones, polyhydroxystyrenes and their derivatives can be used as the resins.

The aromatic hydroxy compounds include, for example, phenol, m-cresol, p-cresol, o-cresol, 2,3-xylenol, 2,5-xylenol, 3,5-xylenol, 3,4-xylenol and other xylenols; m-ethylphenol, p-ethylphenol, o-ethylphenol, 2,3,5- trimethylphenol, 2,3,5-triethylphenol, 4-tert-butylphenol, 3-tert-butylphenol, 2-tert-butylphenol, 2-tert-butyl-4-methylphenol, 2-tert-butyl-5-methylphenol and other alkyl-substituted phenols; p-methoxyphenol, m-methoxyphenol, p-ethoxyphenol, m-ethoxyphenol, p-propoxyphenol, m-propoxyphenol and other alkoxy-substituted phenols; o-isopropenylphenol, p-isopropenylphenol, 2-methyl-4-isopropenylphenol, 2-ethyl-4-isopropenylphenol and other isopropenyl-substituted phenols; phenylphenol and other aryl-substituted phenols; 4,4'-dihydroxybiphenyl, bisphenol A, resorcinol, hydroquinone, pyrogallol and other polyhydroxyphenols. Each of these aromatic hydroxy compounds can be used independently or in combination.

As examples of the aldehydes, there may be mentioned formaldehyde, paraformaldehyde, trioxane, acetaldehyde, propionaldehyde, butyraldehyde, trimethylacetaldehyde, acrolein (acrylaldehyde), crotonaldehyde, cyclohexanealdehyde, furfural, furylacrolein, benzaldehyde, terephthalaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-methylbenzaldehyde, m-methylbenzaldehyde, p-methylbenzaldehyde, o-chlorobenzaldehyde, m-chlorobenzaldehyde, p-chlorobenzaldehyde, cinnamaldehyde and the like. Each of these aldehydes may be used independently or in combination.

Practical examples of the ketones include acetone, methyl ethyl ketone, diethyl ketone and diphenyl ketone. Each of these ketones may be used singly or in combination. Further, a suitable combination of any of aldehydes and any of ketones can be employed.

The condensate of an aromatic hydroxy compound and an aldehyde or a ketone can be prepared in the presence of an acidic catalyst according to a known technique. Such an acidic catalyst includes, for instance, hydrochloric acid, sulfuric acid, formic acid, oxalic acid, p-toluenesulfonic acid and the like.

As examples of the polyhydroxystyrenes and their derivatives, there may be mentioned vinylphenol homopolymers, copolymers of vinylphenol and a copolymerizable comonomer. Such a comonomer includes acrylic acid derivatives, acrylonitrile, methacrylic acid derivatives, methacrylonitrile, styrene, α-methylstyrene, p-methylstyrene, o-methylstyrene, p-methoxystyrene, p-chlorostyrene and other styrene derivatives.

Of these alkali-soluble resins used in the present invention as the ingredient (A), novolak resins obtained from a phenol compound such as m-cresol, p-cresol, 2,5-xylenol, 3,5-xylenol, 2,3,5-trimethylphenol, and an aldehyde such as formaldehyde are advantageously used for their high thermostability. Incidentally, low molecular weight fractions of the novolak resin have been removed. The weight average molecular weight of the novolak resin should range from 2,000 to 25,000, preferably from 2,500 to 20,000 and more preferably from 3,000 to 10,000. The term "weight average molecular weight" as used herein is defined as the value in terms of polystyrene measured by gel permeation chromatography (GPC).

The removal of low molecular weight fractions can be conducted by fractionation or other treatments. The fractionation is carried out by, for example, a process of dissolving a resin obtained by condensation in a good solvent and adding the resultant solution into water to thereby form precipitates. The good solvent includes, for instance, methanol, ethanol and other alcohols, acetone, methyl ethyl ketone and other ketones, ethylene glycol monoethyl ether acetate, and tetrahydrofuran.

The composition of the present invention may be incorporated with an intensifier as necessary. Such an intensifier is not specially restricted and includes any intensifiers conventionally used for positive photosensitive compositions.

Examples of the intensifiers include the hydroxyaryls described in the explanation of the polyphenol compounds, among which preferred are; bis(4-hydroxy-2,3,5-trimethylphenyl)-2-hydroxyphenylmethane, 2,4-bis(3,5-dimethyl-4-hydroxyphenylmethyl)-6-methylphenol, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, 1-[1-(4-hydroxyphenyl)isopropyl]-4-[1,1-bis(4-hydroxyphenyl)ethyl]benzene, 1-[1-(3-methyl-4-hydroxyphenyl)isopropyl]-4-[1,1-bis(3-methyl-4-hydroxyphenyl)ethyl]benzene, 2,6-bis-1(2,4-dihydroxyphenyl)isopropyl]-4-methylphenol, 4,6-bis[1-(4-hydroxyphenyl)isopropyl]resorcin, 4,6-bis(3,5-dimethoxy-4-hydroxyphenylmethyl)pyrogallol, 4,6-bis(3,5-dimethyl-4-hydroxyphenylmethyl)pyrogallol, 2,6-bis(3-methyl-4,6-dihydroxyphenylmethyl)-4-methylphenol, 2,6-bis( 2,3,4-trihydroxyphenylmethyl)-4-methylphenol and 1,1-bis(4-hydroxyphenyl)cyclohexane. Among them, typically preferred are bis(4-hydroxy-2,3,5-trimethylphenyl)-2-hydroxyphenylmethane, bis(4-hydroxy-3,5-dimethylphenyl)-3,4-dihydroxyphenylmethane, 2,4-bis(3,5-dimethyl-4-hydroxyphenylmethyl)-6-methylphenol and 4,6-bis[1-(4-hydroxyphenyl)isopropyl]resorcin.

The compounding ratio of the intensifier may range from 5 to 50% by weight and preferably from 10 to 35% by weight relative to the alkali-soluble resin, i.e., the ingredient (A).

The intensifier may preferably used within the above range in the present invention, because it further enhances the exposure margin, definition and focal depth range properties and improves sensitivity.

In addition to the above specified ingredients, where necessary, the composition of the present invention may further comprise any of compatible additives including, for example, ultraviolet absorbents for inhibition of halation and surfactants for prevention of striation within ranges not adversely affecting the objects of the invention. Examples of the ultraviolet absorbents include 2,2',4,4'-tetrahydroxybenzophenone, 4-dimethylamino-2',4'-dihydroxybenzophenone, 5-amino-3-methyl-1-phenyl-4-(4-hydroxyphenylazo)pyrazole, 4-dimethylamino-4'-hydroxyazobenzene, 4-diethylamino-4'-ethoxyazobenzene, 4-diethylaminoazobenzene and curcumin. As the surfactants, there may be mentioned, for instance, Fluorade FC-430 and FC-431 (trade names, manufactured by Sumitomo 3M Ltd., Japan), F-TOP EF122A, EF122B, EF122C and EF126 (trade names, Tochem Products Ltd., Japan) and other fluorine-containing surfactants.

The positive photosensitive composition of the present invention may preferably used as a solution obtained by dissolving each of the above-specified ingredients in a proper solvent.

Practical examples of the solvent include those used in conventional positive photosensitive compositions, such as acetone, methyl ethyl ketone, cyclohexanone, methyl isoamyl ketone, 2-heptanone and other ketones; ethylene glycol, propylene glycol, diethylene glycol, ethylene glycol monoacetate, propylene glycol monoacetate, diethylene glycol monoacetate, or their monomethyl ethers, monoethyl ethers, monopropyl ethers, monobutyl ethers or monophenyl ethers and other polyhydric alcohols and their derivatives; dioxane and other cyclic ethers; and ethyl lactate, methyl acetate, ethyl acetate, butyl acetate, methyl pyruvate, ethyl pyruvate, methyl methoxypropionate, ethyl ethoxypropionate and other esters. Each of these compounds may be used solely or in combination.

Practically, the composition of the invention may be used, for example, in the following manner: Each of the ingredients (A) and (B) and other ingredients added according to necessity is dissolved in a proper solvent as mentioned above to give a coating solution; the coating solution is then applied, using a spinner or the like, onto a substrate such as a silicon wafer or a substrate on which an adhesion promoter coat or an anti-reflection coating has been formed, and subsequently dried to form a photosensitive film; next, the photosensitive film is irradiated and exposed with an ultraviolet ray source such as a low-pressure mercury lamp, a high-pressure mercury lamp, an ultra-high-pressure mercury lamp or a xenon lamp, through a desired mask pattern, or irradiated with a scanning electron beam; and the exposed portions of the film are then dissolved and removed by applying a developer solution, for example, an alkaline aqueous solution such as a 1 to 10% by weight tetramethylammonium hydroxide (TMAH) aqueous solution, thus forming an image being in exact accordance with the mask pattern.

The present invention will be further illustrated in detail with reference to several inventive examples and comparative examples below which are not directed to limiting the scope of the invention.

Each of the characteristics of the positive photosensitive compositions was evaluated according to the following manner, respectively.

[Exposure Margin]

A sample was applied onto a silicon wafer using a spinner, and dried on a hot plate at 90° C. for 90 sec. to form a resist film having a thickness of 1.05 μm. The resist film was then irradiated for an increasing period from 0.1 sec. at intervals of 0.01 sec. using a reducing-type projection aligner NSR-2005i10D (manufactured by Nikon Corporation, Japan; NA=0.57, δ=0.60). The film was then post-exposure baked (PEB) at 110° C. for 90 sec.; subjected to development in a 2.38% by weight tetramethylammonium hydroxide aqueous solution at 23° C. for 60 sec., washed with water for 30 sec., and dried. In this procedure, the exposure margin was defined as Eop/Eth (ms), where the minimum exposure time period to give an exposed portion having a thickness of 0 after development was defined as Eth (ms), and the minimum exposure time period to obtain a 0.50-μm line and space with a ratio of the line and space of 1:1 was defined as Eop (ms).

[Resolutive Definition]

The resolutive definition was defined as the critical definition at an exposure which reproduced a 0.5-μm mask pattern.

SYNTHETIC EXAMPLE 1

To 100 g of dioxane were added and dissolved 10.00 g (0.0266 mol) of a polyphenol compound (1) represented by the following formula:

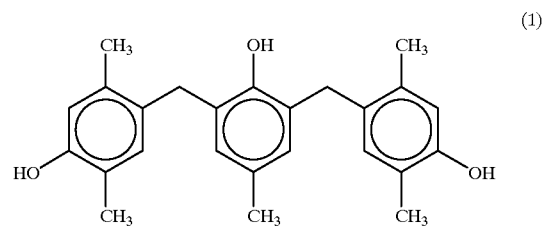

and 14.25 g (0.0532 mol) of naphthoquinone-1,2-diazide-5-sulfonyl chloride (hereinafter simply referred to as 5-NQD) to give Solution A.

In 60 g of dioxane was dissolved monomethyldicyclohexylamine (a) in an amount of 2.0 times as much as the mole of 5-NQD, and the resulting solution was added dropwise to Solution A at a temperature of 20 to 30° C. over 20 minutes.

After the completion of the addition, the mixture was further stirred for 150 minutes and then poured into pure water. As a result, a precipitate was formed. The precipitate was filtered off and the filtrate was washed with pure water to give Ester 1.

Ester 1 was then analyzed by high performance liquid chromatography using a reversed phase column, and found to be composed of 88.49% of a diester, 3.97% of a monoester and 7.54% of triesters. The proportion of by-products was 3.40%.

SYNTHETIC EXAMPLE 2

The procedure of Synthetic Example 1 was repeated except that monocyclohexyldiethylamine (b) was used instead of monomethyldicyclohexylamine (a) to give Ester 2.

The results of analysis by reverse-phase column chromatography are set forth in Table 1.

SYNTHETIC EXAMPLE 3

By using monoethylditert-butylamine (c) instead of monomethyldicyclohexylamine (a), Ester 3 was obtained in a similar manner to Synthetic Example 1.

The results of analysis by reverse-phase column chromatography are set forth in Table 1.

SYNTHETIC EXAMPLE 4

To 100 g of dioxane were added and dissolved 10.00 g (0.02 mol) of a polyphenol compound (2) represented by the following formula:

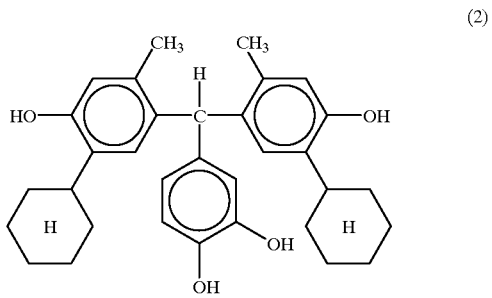

and 10.72 g (0.04 mol) of 5-NQD to give Solution B.

An ester (Ester 4) was obtained in a similar manner to Synthetic Example 1 except that Solution B was used in lieu of Solution A.

The results of analysis by reverse-phase column chromatography are set forth in Table 1.

SYNTHETIC EXAMPLE 5

To 100 g of dioxane were added and dissolved 10.00 g (0.0214 mol) of a polyphenol compound (3) represented by the following formula:

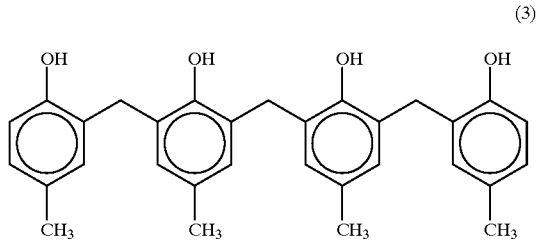

(3)

and 11.45 g (0.0427 mol) of 5-NQD to give Solution C.

The procedure of Synthetic Example 1 was repeated except that Solution C was used instead of Solution A to give Ester 5.

The results of analysis by reverse-phase column chromatography are set forth in Table 1.

SYNTHETIC EXAMPLE 6

Solution D was prepared by dissolving 10.00 g (0.0202 mol) of a polyphenol compound (4) represented by the following formula:

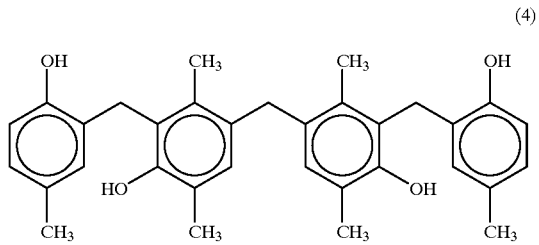

(4)

and 10.81 g (0.0403 mol) of 5-NQD in 100 g of dioxane.

By using Solution D in lieu of Solution A, Ester 6 was obtained in a similar manner to Synthetic Example 1.

The results of analysis by reverse-phase column chromatography are set forth in Table 1.

SYNTHETIC EXAMPLE 7

In 100 g of dioxane were dissolved 10.00 g (0.202 mol) of a polyphenol compound (5) represented by the following formula:

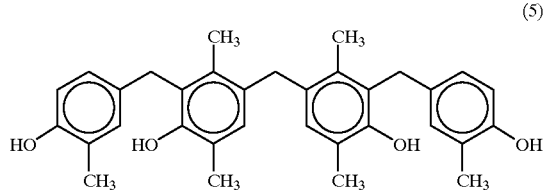

(5)

and 10.81 g (0.0403 mol) of 5-NQD to give Solution E.

Ester 7 was obtained in a similar manner to Synthetic Example 1 except that Solution E was employed instead of Solution A.

The results of analysis by reverse-phase column chromatography are set forth in Table 1.

COMPARATIVE SYNTHETIC EXAMPLE 1

Solution A was prepared in the same manner as in Synthetic Example 1.

In 40 g of dioxane was dissolved triethylamine in an amount of 2.0 times as much as the mole of 5-NQD, and resulting solution was added dropwise to Solution A at a temperature of 20 to 35° C. over 20 minutes.

After the completion of the addition, the mixture was further stirred for 150 minutes and then poured into pure water. As a result, a precipitate was observed. The precipitate was filtered off and the filtrate was washed with pure water to give Ester 8.

The results of analysis by reverse-phase column chromatography are set forth in Table 1.

COMPARATIVE SYNTHETIC EXAMPLE 2

Solution A was prepared in the same manner as in Synthetic Example 1.

In 50 g of dioxane was dissolved N,N-dimethylaniline in an amount of 2.0 times as much as the mole of 5-NQD, and resulting solution was added dropwise to Solution A at a temperature of 20 to 25° C. over 20 minutes.

After the completion of the addition, the mixture was further stirred for 150 minutes and then poured into pure water. As a result, a precipitate was observed. The precipitate was filtered off and the filtrate was washed with pure water to give Ester 9.

The results of analysis by reverse-phase column chromatography are set forth in Table 1.

COMPARATIVE SYNTHETIC EXAMPLE 3

Solution A was prepared in the same manner as in Synthetic Example 1.

In 60 g of dioxane was dissolved dicyclohexylamine in an amount of 2.0 times as much as the mole of 5-NQD, and resulting solution was added dropwise to Solution A at a temperature of 20 to 30° C. over 20 minutes.

After the completion of the addition, the mixture was further stirred for 150 minutes and then poured into pure water, and as a result, a precipitate was observed. The precipitate was filtered off and the filtrate was washed with pure water to give Ester 10.

The results of analysis by reverse-phase column chromatography are set forth in Table 1.

Ester 10 was further washed with pure water several times for the purpose of reducing by-products, but the proportion of the by-products were hardly reduced.

COMPARATIVE SYNTHETIC EXAMPLE 4

Solution B was prepared in the same manner as in Synthetic Example 4.

In 40 g of dioxane was dissolved triethylamine in an amount of 2.0 times as much as the mole of 5-NQD, and resulting solution was added dropwise to Solution B at a temperature of 20 to 35° C. over 20 minutes.

After the completion of the addition, the mixture was further stirred for 150 minutes and then poured into pure water. As a result, a precipitate was observed. The precipitate was filtered off and the filtrate was washed with pure water to give Ester 11.

The results of analysis by reverse-phase column chromatography are set forth in Table 1.

COMPARATIVE SYNTHETIC EXAMPLE 5

Solution C was prepared in the same manner as in Synthetic Example 5.

By using Solution C instead of Solution B, Ester 12 was obtained in a similar manner to Comparative Synthetic Example 4.

The results of analysis by reverse-phase column chromatography are set forth in Table 1.

COMPARATIVE SYNTHETIC EXAMPLE 6

Solution D was prepared in the same manner as in Synthetic Example 6.

Ester 13 was obtained in a similar manner to Comparative Synthetic Example 4 except that Solution D was used instead of Solution B.

The results of analysis by reverse-phase column chromatography are set forth in Table 1.

COMPARATIVE SYNTHETIC EXAMPLE 7

Solution E was prepared in the same manner as in Synthetic Example 7.

Ester 14 was obtained in a similar manner to Comparative Synthetic Example 4 except that Solution E was used instead of Solution B.

The results of analysis by reverse-phase column chromatography are set forth in Table 1.

EXAMPLES 1 TO 7 AND COMPARATIVE EXAMPLES 1 TO 7

A series of positive photosensitive compositions each having the following composition were prepared in a common manner.

Resin: 100 parts by weight of a novolak resin
Intensifier: 25 parts by weight of bis(3,5-dimethyl-4-hydroxyphenol)-2-hydroxyphenylmethane
Photosensitizer: 44 parts by weight of each of the esters obtained in Synthetic Examples 1 to 7 and Comparative Synthetic Examples 1 to 7

Solvent: 470 parts by weight of 2-heptanone

The above-mentioned novolak resin was a novolak resin composed of m-cresol, p-cresol and 2,5-xylenol (4:2:4, by mole) having a weight average molecular weight of 8,500 and a ratio (Mw/Mn) of the weight average molecular weight (Mw) relative to a number-average molecular weight (Mn) of 3.0.

The obtained positive photosensitive compositions were subjected to the above evaluations. The results are shown in Table 2.

TABLE 1

| Syn. Ex. | Ester | Polyphenol Compound | Catalyst | By-product (%) | Diester (%) |
|---|---|---|---|---|---|
| 1 | 1 | (1) | (a) | 3.40 | 86.84 |
| 2 | 2 | (1) | (b) | 3.45 | 81.62 |
| 3 | 3 | (1) | (c) | 3.33 | 78.93 |
| 4 | 4 | (2) | (a) | 0.34 | 87.36 |
| 5 | 5 | (3) | (a) | 0 | 83.06 |
| 6 | 6 | (4) | (a) | 1.86 | 94.56 |
| 7 | 7 | (5) | (a) | 0 | 79.61 |
| Comp. Syn. Ex. 1 | 8 | (1) | Triethylamine | 4.62 | 72.39 |
| 2 | 9 | (1) | N,N-dimethyaniline | — | — |
| 3 | 10 | (1) | Dicyclohexylamine | 10.31 | 93.01 |
| 4 | 11 | (2) | Triethylamine | 2.41 | 77.71 |
| 5 | 12 | (3) | Triethylamine | 0 | 73.07 |
| 6 | 13 | (4) | Triethylamine | 2.20 | 89.41 |
| 7 | 14 | (5) | Triethylamine | 0 | 65.80 |

\* No ester was obtained (the reaction did not proceed) in Comparative Synthetic Example 2. The term "Diester (%)" indicates a ratio of the peak area of the diester relative to the total of peak areas of esters, and the term "By-product (%)" indicates a ratio of the peak areas of other products than esters relative to the total peak areas of the esters and the other products, both in reverse-phase column chromatography.

TABLE 2

| | Photosensitizer Ester | Exposure Margin (Eop/Eth) | Resolutive Definition ($\mu$m) |
|---|---|---|---|
| Example | | | |
| 1 | 1 | 2.30 | 0.30 |
| 2 | 2 | 2.25 | 0.32 |
| 3 | 3 | 2.25 | 0.32 |
| 4 | 4 | 1.80 | 0.38 |
| 5 | 5 | 2.50 | 0.30 |
| 6 | 6 | 2.20 | 0.30 |
| 7 | 7 | 2.20 | 0.28 |

TABLE 2-continued

|  | Photosensitizer Ester | Exposure Margin (Eop/Eth) | Resolutive Definition (μm) |
|---|---|---|---|
| Comp. Ex. | | | |
| 1 | 8 | 2.20 | 0.35 |
| 2 | 9 | — | — |
| 3 | 10 | 2.10 | 0.38 |
| 4 | 11 | 1.70 | 0.40 |
| 5 | 12 | 2.40 | 0.32 |
| 6 | 13 | 2.10 | 0.30 |
| 7 | 14 | 2.10 | 0.30 |

As evident from the above results of Examples and Comparative Examples, the present invention provides a process for producing a polyphenol diester by which a diester of any of various polyphenol compounds can be obtained with ease in a good yield without the use of specific polyphenol compounds, and a positive photosensitive composition using the diester which can achieve a high definition and a satisfactory exposure margin.

While the invention has been described in detailed with reference to specific embodiments thereof, it will be apparent one of ordinary skill in the art that various changes and modifications can be made therein without departing from the spirit and scope thereof.

What is claimed is:

1. A process for producing a polyphenol diester which comprises the step of esterifying a polyphenol compound having 2 to 10 phenolic hydroxyl groups and having a molecular weight of equal to or less than 1,000 with a naphthoquinone-1,2-diazidesulfonyl halide in the presence of a compound represented by the following formula (I) or (II):

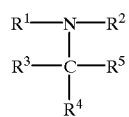
(I)

-continued

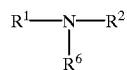
(II)

wherein each of $R^1$, $R^3$, $R^4$ and $R^5$ is independently an alkyl group, alkenyl group or alkoxy group each having from 1 to 4 carbon atoms, $R^2$ is an alkyl group, alkenyl group or alkoxy group each having from 1 to 10 carbon atoms or a cycloalkyl group having from 3 to 10 carbon atoms, and $R^6$ is an alkyl group or cycloalkyl group each having from 5 to 10 carbon atoms.

2. The process according to claim 1, wherein the compound represented by the formula (II) is a compound represented by the following formula (III):

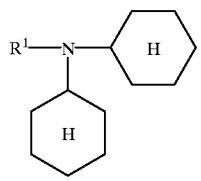
(III)

wherein $R^1$ has the same meaning as defined above.

3. The process according to claim 2, wherein the compound represented by the formula (II) is monomethyldicyclohexylamine.

4. The process according to claim 1, wherein the compound represented by the formula (I) is at least one compound selected from the group consisting of monoethylditert-butylamine, N,N-dimethyl-1,1-diemthylpropylamine, N-ethyl-N-methyl-1,1-methylethyl-butylamine, N-cyclohexyl-N-ethyl-1,1-diethyl-pentylamine, N-ethoxy-N-propyl-1,1-diethyl-pentylamine.

5. The process according to claim 1, wherein The amount of the compound represented by the formula (I) or (II) fall in the range from 0.8 to 4.0 moles per mole of naphthoquinone-1,2-diazidesulfonyl halide.

6. A positive photosensitive composition comprising:
(A) an alkali-soluble resin, and
(B) a polyphenol diester produced by the process of either claim 1 or 2.

* * * * *

UNITED STATES PATENT AND TRADEMARK OFFICE
CERTIFICATE OF CORRECTION

PATENT NO. : 6,106,994
DATED : August 22, 2000
INVENTOR(S) : Niikura, Satoshi et al.

It is certified that error appears in the above-identified patent and that said Letters Patent is hereby corrected as shown below:

Claim 4:
Line 5, change "diemthylpropylamine" to --dimethylpropylamine--.

Claim 5:
Line 1, change "The amount" to --the amount--.

Signed and Sealed this

Twelfth Day of June, 2001

*Attest:*

*Attesting Officer*

NICHOLAS P. GODICI
*Acting Director of the United States Patent and Trademark Office*